United States Patent [19]

Bühlmann et al.

[11] 4,451,458
[45] May 29, 1984

[54] METHOD FOR THE TREATMENT OF POST-OPERATIVE THROMBOSIS

[75] Inventors: Hans Bühlmann; Dieter Welzel, both of Nüremberg, Fed. Rep. of Germany

[73] Assignee: Sandoz Ltd., Basel, Switzerland

[21] Appl. No.: 379,272

[22] Filed: May 17, 1982

Related U.S. Application Data

[63] Continuation of Ser. No. 119,583, Feb. 7, 1980, abandoned, which is a continuation of Ser. No. 942,807, Sep. 15, 1978, abandoned, which is a continuation of Ser. No. 890,165, Mar. 27, 1978, abandoned, which is a continuation-in-part of Ser. No. 703,256, Jul. 7, 1976, abandoned.

[51] Int. Cl.³ ............... A61K 31/725; A61K 31/48
[52] U.S. Cl. ................................. 424/183; 424/261
[58] Field of Search ........................................ 424/183

[56] References Cited

PUBLICATIONS

*Med. Klin.* 70 (1975), 1553, (No. 39).
*Chemical Abstracts,* vol. 72, 130867k, (1970).
*Deutche Med. W.* 100, 2065-2069, Oct. 1975.
Bergogue-Revue de l'Atheroscleroso, (Paris), 10 (2), 11-13 (1968).
Mohe, et al.-"Sonderdruck aus der Klinik Arzt", Heft 3/75, Thrombose Prophylaxe, pp. 3-12.
*Lancet,* 45, 1975, pp. 45-51, 63 and 64.
Kakkar-Special Article of *Circulation* vol. 51, Jan. 1975, pp. 8-19.

*Primary Examiner*—Frederick E. Waddell
*Attorney, Agent, or Firm*—Gerald D. Sharkin; Robert S. Honor

[57] ABSTRACT

The invention provides novel pharmaceutical compositions useful in the treatment of thrombosis in mammals, comprising a mixture of dihydroergotamine or a related ergot alkaloid and heparin.

3 Claims, No Drawings

METHOD FOR THE TREATMENT OF POST-OPERATIVE THROMBOSIS

This is a continuation of application Ser. No. 119,583, filed Feb. 7, 1980, which in turn is a continuation of application Ser. No. 942,807, filed Sept. 15, 1978, which in turn is a continuation of application Ser. No. 890,165, filed Mar. 27, 1978, all now abandoned.

This invention relates to new pharmaceutical compositions containing compounds of formula 1:

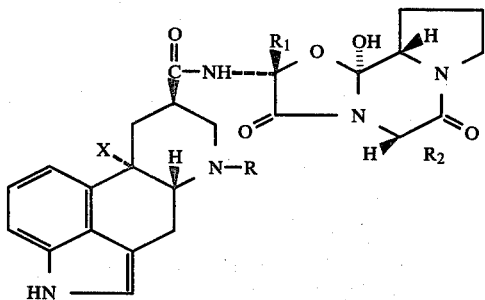

in which
R is hydrogen or alkyl having from 1 to 4 carbon atoms, other than t.-butyl
$R_1$ is methyl, ethyl or isopropyl
$R_2$ is isopropyl, sec.-butyl, isobutyl or benzyl
and
X is hydrogen or methoxy.

The invention provides a pharmaceutical composition comprising a mixture of a compound of formula I and heparin, in association with a pharmacologically acceptable diluent or carrier.

By the terms "compounds of formula I" and "heparin" are included pharmacologically acceptable salts of these compounds. A pharmacologically acceptable salt is one which does not have substantially higher toxicity than the corresponding free acid or base. Examples of such salts are the methanesulfonate, maleate and tartrate salts of compounds of formula I, and the sodium, potassium and calcium salts of heparin.

Preferred compounds of formula I are dihydroergotamine, in which R=methyl, $R_1$=methyl, $R_2$=benzyl and X=hydrogen; 6-nor-6-isopropyl-9,10-dihydro-2'$\beta$-methyl-5'$\alpha$-benzylergopeptin and dihydroergovaline, especially dihydroergotamine.

Pharmacologically acceptable diluents and carriers include polymers for example polyvinyl pyrrolidone and organic esters, particularly esters of $C_{10}$–$C_{24}$ fatty acids, including natural plant oils.

The proportion of compound of formula I (in mg) to heparin (in international units, I.U.) is suitably 1:500 to 1:70,000, preferably 1:2000 to 1:20,000.

The invention also provides a process for the preparation of a pharmaceutical composition according to the invention, characterised by mixing a compound of formula I and heparin together with a pharmaceutically acceptable diluent or carrier.

Preferred processes according to the invention are:
(a) working up a compound of formula I with a pharmaceutically acceptable polymer, preferably polyvinylpyrrolidone, to obtain a solid material which is then mixed with heparin, or (b) suspending a compound of formula I together with heparin in a pharmaceutically acceptable organic liquid, preferably an organic ester.

Process (a) is preferably carried out by mixing the compound of formula I together with polyvinylpyrrolidone in the form of an uncrosslinked poly-N-vinyl-2-pyrrolidone of average molecular weight from 10,000 to 100,000, preferably from 11,500 to 40,000, particularly 25,000, optionally together with pharmacologically acceptable additives. Such additives may include surfactants, for example polyethylene glycol fatty acid esters, particularly polyethylene glycol stearate, as well as stabilizing additives for example acids, particularly methanesulphonic acid, maleic acid and tartaric acid, to maintain a pH of less than 7, preferably 4–5. The proportion of compound of formula I in the total mixture together with the optional additives, is suitably from 0.1 to 5% preferably from 0.5 to 1.0% by weight.

The mixture is then worked up so as to obtain a dry homogeneous material, for example by dissolving in a suitable solvent, and evaporating the solution. Suitable solvents include alcohols having from 1 to 4 carbon atoms, for example methanol and ethanol. The mixture may suitably be dissolved at an elevated temperature, preferably from 30° to 80° C., more preferably from 40° to 70° C. After complete solution, the solvent may be evaporated under the above conditions of temperature; preferably initially under atmospheric pressure and finally under vacuum. Optionally, only a part of the polyvinylpyrrolidone and/or the further additives may be added to the compound of formula I before the solution is prepared, and the addition of the remainder may take place during the evaporation stage. The solid residue obtained by complete removal of the solvent and cooling to room temperature (15°–25° C.) may be ground to a fine powder in conventional manner and dried for example in vacuo for 12 hours at 30° C.

The dried product is then mixed with the corresponding quantity of heparin, to give a solid product which may be dissolved in sterile distilled water to provide an injectable solution. Preferably this injectable solution will be isotonic and buffered to a physiologically acceptable pH. In order to accomplish this, the solid product is preferably mixed with sodium chloride and/or sodium hydrogen phosphate in quantity sufficient to give an isotonic solution of pH 7–7.5 when dissolved in the volume of water required to give the desired concentration of active ingredients.

Process (b) may be carried out by suspending the compound of formula I together with heparin in an organic ester, suitably isopropyl myristate, isopropyl palmitate, ethyl oleate, olive oil, peanut oil, seasame oil and other common plant oils, or mixtures of these.

For a mixture of from 0.1 to 2 mg compound of formula I and 1000 to 7000 I.U. heparin, a quantity of from 0.3 to 10 ml of organic ester may be used. Preferably a mixture of 0.5 mg dihydroergotamine methanesulfonate and 5000 I.U. sodium heparin is suspended in 1 ml isopropyl myristate. The suspension is preferably prepared by stirring at room temperature (15°–25° C.).

The pharmaceutical compositions according to the invention have surprisingly good antithrombotic properties, as shown by the $I^{125}$-fibrinogen uptake test of K. H. Frey et al (Med. Klin. 70 (1975) pp 1553–1558), in which radiation from $I^{125}$-fibrinogen, which is selectively concentrated in thrombotic material in leg veins, is measured externally in human patients.

In this test, patients undergoing major surgery, for example total hip replacement, receive 100 μci of $I^{125}$-fibrinogen parenterally the day before surgery and their legs are scanned for $I^{125}$ radiation each day for between 2 and 3 weeks thereafter. The fibrinogen injection is repeated after 8–10 days if the count rate remains low. A Logic 121 counter/ratemeter is used for recording radioactivity, counting being performed according to the technique of Kakkar et al. (*Lancet* 1970, 1, 540). Deep vein thrombosis (DVT) is diagnosed if the counts at any site differ by 20% or more from those at an adjacent point on the same leg or the same position on the opposite leg, and if this difference persists or increases in the subsequent 24 hours. The incidence of DVT in patients receiving prophylaxis by administration of a compound of formula I in conjunction with heparin is compared with that of control groups receiving heparin prophylaxis or no prophylaxis.

The compositions are therefore indicated for antithrombotic use, particularly in prophylaxis of postoperative thrombosis in mammals. A suitable indicated daily dosage is from 0.2 to 4 mg, preferably from 0.5 to 2 mg compound of formula I and from 2000 to 14,000 I.U., preferably from 4000 to 10,000 I.U. heparin. This daily dosage may suitable be administered in divided dosages of from 0.05 to 2 mg, preferably 0.125 to 1 mg compound of formula I and from 500 to 7,000 I.U., preferably from 1000 to 5000 I.U. heparin, two to four times daily. Particularly preferred is a mixture of 0.5 mg dihydroergotamine methansulfonate and 5000 I.U. sodium heparin, administered thrice daily. The active ingredients may also be administered separately.

The invention further provides galenic preparations of the compositions according to the invention, for example sterile injectable solutions or suspensions for parenteral administration. Such galenic forms may be prepared from the compositions according to the invention in conventional manner.

The compositions themselves, or galenic preparations thereof, may suitably be packaged in unit dosage forms, for example ampules of sterile injectable suspension containing a unit dosage of the active ingredients.

The following Examples illustrate the invention:

EXAMPLE 1

Dry mixture to make up injectable solution

Dihydroergotamine methanesulfonate (4.0 g) and 476 g polyvinyl pyrrolidone (average MW 25,000) is added to 1600 ml methanol in a 4 l flask. The flask is connected to a rotary evaporator, and rotated in a bath at 60° C. until the flask contents reach approximately 60° C. A clear solution is obtained.

The solvent is then evaporated under reduced pressure (ca. 250 Torr) at a bath temperature of 60° C., until the residue in the flask has a syrupy consistency. The residue is transferred to an evaporating dish and left to stand for two hours at room temperature. The solid residue is dried in a vacuum oven at 30° C., ca. 1 Torr for 12 hours, then milled and redried.

The dried residue (480 g) is then mixed under aseptic conditions with a quantity of sodium heparin corresponding to 40,000,000 I.U., 8 g disodium hydrogen phosphate dihydrate and 72 g sodium chloride, specially purified. The mixture is then made up in bottles of unit dosage scaled with a pierceable septum, each bottle containing 105 mg of the dry mixture, comprising 0.5 mg dihydroergotamine methanesulfonate and 5000 I.U. (essentially equivalent to 5000 U.S.P.) sodium heparin.

In use, the septum is pierced by the needle of a syringe containing 1 ml of sterile distilled water which is injected into the bottle. When the solid mixture has dissolved, the solution is withdrawn into the syringe and administered parenterally.

EXAMPLE 2

Suspension

Dihydroergotamine methansulfonate (0.5 g) and a quantity of sodium heparin corresponding to 5,000,000 I.U. are dispersed in 1 l of sterile filtered isopropyl myristate by stirring under aseptic conditions. Ampoules of 1 ml capacity are then filled with the suspension.

EXAMPLES 3, 4

Examples 1 and 2 are repeated using in place of dihydroergotamine methanesulfonate an equivalent quantity of 6-nor-6-isopropyl-9,10-dihydro-2'$\beta$-methyl-5-$\beta$-benzylergopeptin methanesulfonate.

EXAMPLES 5, 6

Examples 1 and 2 are repeated using instead of dihydroergotamine methanesulfonate an equivalent quantity of dihydroergovaline methanesulfonate.

EXAMPLE 7

Clinical data

In a clinical study on human patients, of 82 consecutive patients undergoing total hip replacement, 25 received 5,000 I.U. heparin together with 0.5 mg dihydroergotamine parenterally two hours before surgery and then every 8 hours for the next 10 days. A further group of 25 received 5,000 I.U. ($\approx$U.S.P.) heparin according to the same regimen without DHE, and a control group of 32 patients received no prophylaxis.

Of the control group, 22 patients (69%) developed deep vein thrombosis (DVT) as determined by the $I^{125}$-fibrinogen uptake test. For the group receiving heparin alone, the incidence of DVT was 8 patients (32%) and for the group receiving heparin plus dihydroergotamine the incidence of DVT was 4 patients (16%).

EXAMPLE 8

Example 1 is repeated using a quantity of sodium heparin corresponding to 20,000,000 I.U., the quantities of the other components remaining the same. The bottles of unit dosage each contain approx. 90 mg of the dry mixture, comprising 0.5 mg dihydroergotamine methanesulphonate and 2500 I.U. ($\approx$U.S.P.) sodium heparin.

What is claimed is:

1. A method for the prophylactic treatment of post-operative thrombosis in mammals, comprising parenterally administering dihydroergotamine in conjunction with heparin, wherein the administration is effected with a unit dose comprising about 0.5 mg. of dihydroergotamine and about 2500–5000 I.U. of heparin and said doses are administered two to four times daily.

2. A pharmaceutical composition useful in the prophylactic treatment of post-operative thrombosis in mammals, comprising in unit dosage form about 0.5 mg. of dihydroergotamine and about 2500–5000 I.U. of heparin.

3. A pharmaceutical composition useful in the prophylactic treatment of post-operative thrombosis in mammals, comprising in unit dosage form about 0.5 mg. of dihydroergotamine and about 5000 I.U. of heparin.

* * * * *